United States Patent
Kim et al.

(10) Patent No.: US 11,826,474 B2
(45) Date of Patent: Nov. 28, 2023

(54) NANO-LIPID CARRIER FOR ENCAPSULATION OF BIOACTIVE MATERIAL, AND METHOD FOR PRODUCING SAME

(71) Applicant: BINOTEC CO., LTD., Daegu (KR)

(72) Inventors: Yu Mi Kim, Daegu (KR); Gi Hyun Jang, Daegu (KR)

(73) Assignee: BINOTEC CO., LTD., Daegu (KR)

( * ) Notice: Subject to any disclaimer, the term of this patent is extended or adjusted under 35 U.S.C. 154(b) by 3 days.

(21) Appl. No.: 17/279,551

(22) PCT Filed: Dec. 3, 2019

(86) PCT No.: PCT/KR2019/016916
§ 371 (c)(1),
(2) Date: Mar. 24, 2021

(87) PCT Pub. No.: WO2020/116892
PCT Pub. Date: Jun. 11, 2020

(65) Prior Publication Data
US 2021/0338594 A1 Nov. 4, 2021

(30) Foreign Application Priority Data
Dec. 7, 2018 (KR) .................. 10-2018-0157119

(51) Int. Cl.
| | |
|---|---|
| *A61K 9/50* | (2006.01) |
| *A61P 17/14* | (2006.01) |
| *A61K 9/48* | (2006.01) |
| *A61K 38/06* | (2006.01) |

(52) U.S. Cl.
CPC .......... *A61K 9/5015* (2013.01); *A61K 9/4858* (2013.01); *A61K 9/5089* (2013.01); *A61K 38/06* (2013.01); *A61P 17/14* (2018.01)

(58) Field of Classification Search
CPC .. A61K 9/5015; A61K 9/4858; A61K 9/5089; A61K 38/06; A61K 17/14; A61K 8/553; A61K 8/64; A61K 8/8147; A61K 9/0014; A61K 9/1075; A61K 47/14; A61K 2800/413; A61K 8/11; A61K 9/5123; A61K 9/5192; A61K 2800/56; A61K 2800/805; A61Q 19/00
See application file for complete search history.

(56) References Cited

FOREIGN PATENT DOCUMENTS

| | | | |
|---|---|---|---|
| CN | 108785141 A | | 11/2018 |
| CN | 108938456 A | * | 12/2018 |
| JP | 2002-544155 A | | 12/2002 |
| KR | 10-2007-0091443 A | | 9/2007 |
| KR | 10-1054731 B1 | | 8/2011 |
| KR | 10-1377710 B1 | | 3/2014 |
| KR | 10-1810160 B1 | | 1/2018 |
| KR | 10-1851388 B | | 6/2018 |
| KR | 10-2018-0097368 A | | 8/2018 |
| KR | 10-2037354 B1 | | 10/2019 |
| WO | WO 2011/116963 A2 | | 9/2011 |
| WO | WO-2019024841 A1 | * | 2/2019 ........... A61K 31/704 |

OTHER PUBLICATIONS

Supplementary European Search Report dated Aug. 9, 2022, issued to European Application No. 19893929.0.

* cited by examiner

*Primary Examiner* — Jessica Worsham
(74) *Attorney, Agent, or Firm* — Stein IP, LLC

(57) ABSTRACT

The present invention relates to a particulate nano-lipid carrier for the encapsulation of a bioactive material, and a method for producing same, and more specifically, to a particulate nano-lipid carrier having excellent nanoparticle stability and improved encapsulation of water-soluble drugs. A nano-lipid carrier according to the present invention has significantly improved bioactive material stability and encapsulation efficiency compared to conventional carriers, and it is anticipated that the nano-lipid carrier according to the present invention will be immediately commercializable as a raw material for cosmetics by means of a hair follicle targeting production method suitable for mass production.

6 Claims, 3 Drawing Sheets ly used in the fields of drug delivery and cosmetics. However, the transdermal carriers tend to have a significantly low delivery capability into the epidermis, compared to the theoretical delivery capability, and have very low stability as the colloidal carrier. Therefore, there is an urgent need for solutions to the above problems.

NANO-LIPID CARRIER FOR ENCAPSULATION OF BIOACTIVE MATERIAL, AND METHOD FOR PRODUCING SAME

CROSS-REFERENCE TO RELATED APPLICATIONS

This application is a national stage of International Application No. PCT/KR2019/016916, filed Dec. 3, 2019, which claims the benefit of Korean Application No, 10-2018-0157119, filed Dec. 7, 2018, in the Korean Intellectual Property Office, the disclosures of which are incorporated herein by reference.

TECHNICAL FIELD

This invention relates to a nano-lipid carrier for encapsulation of a bioactive material and a method for producing the same. More particularly, the present invention relates to a particulate nano-lipid carrier having excellent nanoparticle stability and improved encapsulation of water-soluble drugs.

BACKGROUND ART

The development of a drug delivery system capable of efficiently delivering a drug into the human body has its growing importance. Technology for encapsulating a drug in a drug delivery system into a micro- or nano-sized carrier and making use of such a carrier may be widely used for injection, oral or transdermal delivery, or the like. Representative technology includes structures in the form of an emulsion, a liposome, microparticles, or nanoparticles.

The emulsion has a structure in which a drug is encapsulated in oil droplets and dispersed using an amphiphilic surfactant, and thus is very effective in dissolving poorly soluble drugs, but has low physical stability. The liposome has advantages in that it may circulate as a colloidal nanocarrier in blood for a long period of time, is biocompatible, and reduces the toxicity of a bioactive material, but has drawbacks in that it has a high possibility of loss by the phagocytosis of macrophages, and is colloidally unstable. Also, the polymeric microparticles or nanoparticles have advantages in that they are favorable for controlling the release of drugs, targeting, and the like, and their size may be adjusted to a desired particle size to prepare various types of particles, but have drawbacks in that they have cytotoxicity, removal of an organic solvent is required when the solvent is used, and their mass production is difficult.

In recent years, solid-phase lipid nanoparticles which have overcome the drawbacks of such drug delivery systems have been actively researched as a novel structure. The solid-phase lipid nanoparticles have a structure in which a drug is present in a state in which the drug is encapsulated in solid lipids because the drug is encapsulated using the lipids in a solid phase at room temperature to produce spherical particles. The solid-phase lipid nanoparticles are favorable for encapsulating a hydrophobic drug because solid lipids are mixed with a hydrophobic drug while heating the solid lipids, and then cooled in an aqueous phase while forming particles using a surfactant. However, the solid-phase lipid nanoparticles have a drawback in that the hydrophilic drugs such as peptides have a very low encapsulation rate of 20% to 30%. To solve the above problem, a method for combining the hydrophilic drug with hydrophobic nanoparticles or producing the hydrophilic drug in the form of an emulsion, a method for combining lipids in a liquid crystal phase, and the like have been researched. However, such methods still have problems in that a striking improvement of an encapsulation rate is not realized, and it is difficult to mass-produce the solid-phase lipid nanoparticles.

Among the routes for drug delivery, methods for delivering a drug to the skin in a noninvasive fashion mainly include a route for transdermal delivery and a route for hair follicle delivery. The results of research conducted so far show that, when a carrier is manufactured in a nanosize, the probability of the carrier passing between keratinocytes to be absorbed into the dermis is much higher than the carriers having a microsize or larger size. Representative transdermal carriers include liposomes used to encapsulate a drug with phospholipids, and are widely used in the fields of drug delivery and cosmetics. However, the transdermal carriers tend to have a significantly low delivery capability into the epidermis, compared to the theoretical delivery capability, and have very low stability as the colloidal carrier. Therefore, there is an urgent need for solutions to the above problems.

SUMMARY OF INVENTION

Technical Problem

Unlike conventional solid-phase lipid nanoparticles, which have been mainly used as only a carrier for a fat-soluble bioactive material because the conventional solid-phase lipid nanoparticles have low encapsulation efficiency for water-soluble bioactive materials, a technical objective of the present invention is to use a nano-lipid carrier as a carrier for a water-soluble bioactive material, thereby significantly improving the encapsulation efficiency of the water-soluble bioactive materials.

Another technical objective of the present invention is to solve the problem of rapid release of a water-soluble bioactive material as a structure of the solid-phase lipid nanoparticles collapses due to low stability even when the bioactive material is encapsulated in the solid-phase lipid nanoparticles, to provide a nano-lipid carrier capable of stably encapsulating the water-soluble bioactive material, and to provide a nano-lipid carrier capable of stably exhibiting colloidal stability for a long period of time even when present in the form of an aqueous dispersion.

Yet another technical objective of the present invention is to provide solid-phase lipid nanoparticles having superior absorption efficiency specific for hair follicles when the skin is treated with the solid-phase lipid nanoparticles.

Solution to Problem

A method for producing a nano-lipid carrier having a bioactive material encapsulated therein according to the present invention includes: generating an aqueous hydrophilic polymer complex solution including a bioactive material and a hydrophilic polymer; introducing the aqueous hydrophilic polymer complex solution into a phospholipid solution to generate a colloidal solution; introducing the colloidal solution into lipids to generate a water-in-oil dispersion; and introducing the water-in-oil dispersion into an aqueous solution including a surfactant, followed by homogenization to generate a nano-lipid carrier.

In the method for producing a nano-lipid carrier according to one embodiment of the present invention, the bioactive material may include a peptide-based compound.

In the method for producing a nano-lipid carrier according to one embodiment of the present invention, the bioactive material may have a positive or negative charge in an aqueous solution.

In the method for producing a nano-lipid carrier according to one embodiment of the present invention, the hydrophilic polymer may include an anionic or cationic polymer, and may have a charge different from that of the bioactive material.

In the method for producing a nano-lipid carrier according to one embodiment of the present invention, the aqueous hydrophilic polymer complex solution may exhibit hydrogel properties.

In the method for producing a nano-lipid carrier according to one embodiment of the present invention, the lipids may include two or more lipids having different melting points.

In the method for producing a nano-lipid carrier according to one embodiment of the present invention, the mixed lipid solution may include a first lipid which is in a solid phase at room temperature, and a second lipid which is in a liquid phase at room temperature.

In the method for producing a nano-lipid carrier according to one embodiment of the present invention, the water-in-oil dispersion may be prepared by heating the lipids to form a solution phase, followed by mixing of the colloidal solution.

In the method for producing a nano-lipid carrier according to one embodiment of the present invention, the surfactant may include an aliphatic glyceryl-based compound.

In the method for producing a nano-lipid carrier according to one embodiment of the present invention, a solvent of the phospholipid solution may include an alcohol.

In the method for producing a nano-lipid carrier according to one embodiment of the present invention, the colloidal solution may include an ethosomal colloid.

In the method for producing a nano-lipid carrier according to one embodiment of the present invention, the generating of the nano-lipid carrier may further include a high-pressure emulsification step.

Also, a nano-lipid carrier according to the present invention includes a core portion including a hydrophilic polymer complex containing a bioactive material and a hydrophilic polymer; and a shell portion disposed on a surface of the core portion and including lipids, wherein the core portion further includes phospholipids.

In the nano-lipid carrier according to one embodiment of the present invention, the lipids and the phospholipids may be included at a weight ratio of 100:0.1 to 100:50.

In the nano-lipid carrier according to one embodiment of the present invention, the bioactive material and the hydrophilic polymer may be included at a weight ratio of 2,000:1 to 20:1.

In the nano-lipid carrier according to one embodiment of the present invention, the nano-lipid carrier may have an average particle size of 20 nm to 1,000 nm, and may satisfy the following Relationship 1:

$$|T_0 - T_{20}|/T_0 < 0.2 \quad \text{[Relationship 1]}$$

(wherein T0 represents a transmittance measured at a wavelength of 500 nm after an aqueous dispersion including 1% by weight of a nano-lipid carrier is prepared, and T20 represents a transmittance measured at a wavelength of a 500 nm after the aqueous dispersion including 1% by weight of a nano-lipid carrier is left at 45° C. for 20 days.)

In addition, the present invention provides a cosmetic composition including the nano-lipid carrier.

The cosmetic composition according to one embodiment of the present invention may have hair follicle targeting properties, and may be a cosmetic composition for transdermal absorption.

Further, the present invention provides a method for delivering a nano-lipid carrier, which has a bioactive material encapsulated therein, in a hair follicle targeting fashion, wherein the method includes treating the skin with the nano-lipid carrier.

Advantageous Effects of Invention

A nano-lipid carrier according to the present invention can have a high content of a water-soluble bioactive material encapsulated therein, and thus can be preferably used as a carrier for the water-soluble bioactive material.

Also, the nano-lipid carrier according to the present invention can be used to stably encapsulate the water-soluble bioactive material, and can stably exhibit colloidal stability for a long period of time even when present in the form of an aqueous dispersion.

Further, the nano-lipid carrier according to the present invention can have a superior absorption rate specific for hair follicles when the skin is treated with the solid-phase lipid nanoparticles, and can be mass-produced by a relatively simple production method, and thus can be preferably used as a pharmaceutical composition or a cosmetic composition for delivering a bioactive material to hair follicles.

DETAILED DESCRIPTION OF EMBODIMENT

Figure 1:
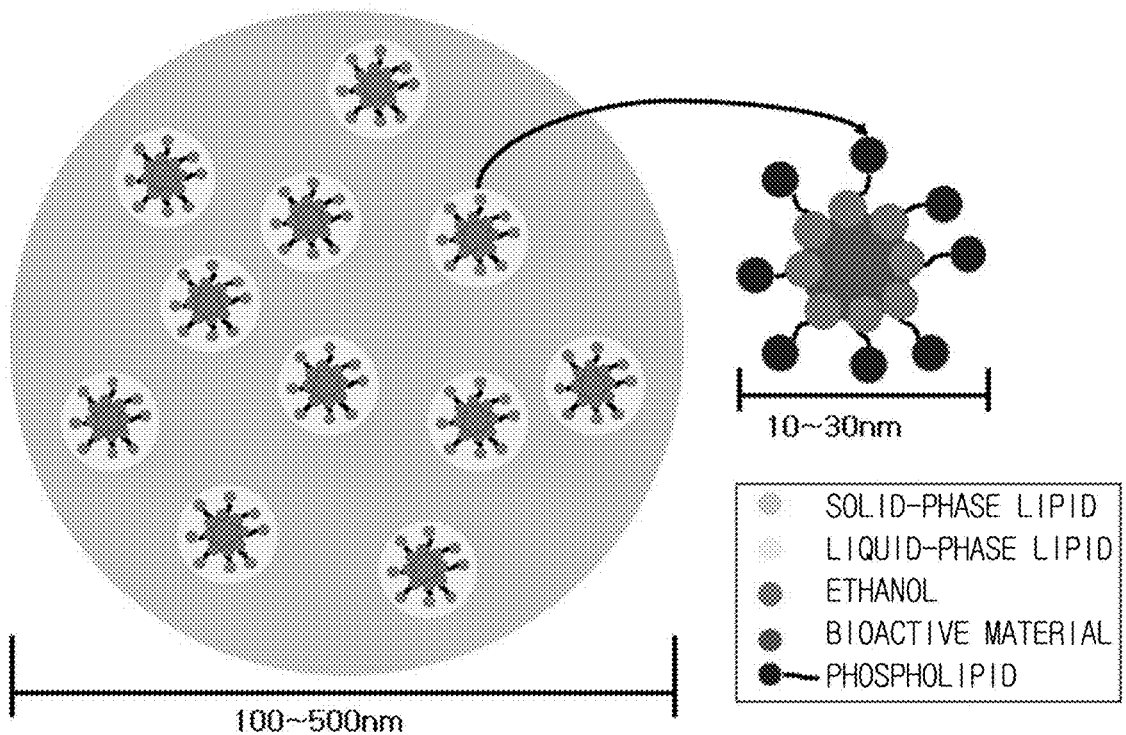
FIG. 1 is a schematic diagram showing a structure of a nano-lipid carrier having a bioactive material encapsulated therein according to one embodiment of the present invention.

Hereinafter, the present invention will be described in detail with reference to the accompanying drawings. The drawings presented herein below are provided as one example to sufficiently provide the scope of the present invention to those skilled in the art. Therefore, it should be understood that the present invention may be embodied in various forms, but is not intended to be limited to the drawings presented herein below. In this case, the drawings presented herein below may be shown in an exaggerated manner to make the scope of the present invention more clearly apparent.

Unless otherwise defined, technical and scientific terms used in this specification of the present invention have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In the following description and the accompanying drawings, a description of known functions and configurations, which unnecessarily obscure the subject matter of the present invention, will be omitted.

Also, the singular forms "a," "an," and "the" used in the specification of the present invention are intended to also encompass plural forms unless the context clearly dictates otherwise.

In addition, the units used without any particular comments in the specification of the present invention and the appended claims are based on weight. For example, the units of % or percentage refer to a percent (%) by weight or weight percentage.

Additionally, unless otherwise defined in this specification of the present invention, a molecular weight of a polymer refers to a weight average molecular weight of the polymer.

Also, unless otherwise defined in this specification of the present invention, an average particle size of particles refers to D50 obtained by a particle size analyzer.

Furthermore, in the specification of the present invention, the term "comprise(s)" is intended to be open-ended transitional phrases having an equivalent meaning with "contain(s)," "include(s)," "have," "has," and "is(are) characterized by," and does not exclude elements, materials, or steps, which are not further listed. Also, the expression "consist(s) essentially of" means that one element, material or step, which is not listed in combination with the other elements, materials or steps, may be present at an amount having no unacceptably significant influence on at least one basic and novel technical idea of the present invention. Also, the expression "consist(s) of" means the presence of only listed the elements, materials or steps.

Further, in the specification of the present invention, a hydrogel refers to a solid material that includes a hydrophilic polymer having a swelling property when water is used as a solvent, and also refers to a material that is not substantially deformed or has low fluidity because it has high viscosity.

Hereinafter, a method for producing a nano-lipid carrier having a bioactive material encapsulated therein according to the present invention will be described in detail The present invention provides a method for producing a nano-lipid carrier having a bioactive material encapsulated therein, which includes: generating an aqueous hydrophilic polymer complex solution including a bioactive material and a hydrophilic polymer; introducing the aqueous hydrophilic polymer complex solution into a phospholipid solution to generate a colloidal solution; introducing the colloidal solution into lipids to generate a water-in-oil dispersion; and introducing the water-in-oil dispersion into an aqueous solution including a surfactant, followed by homogenization to generate a nano-lipid carrier.

In the generating of the aqueous hydrophilic polymer complex solution including the bioactive material and the hydrophilic polymer, the bioactive material may be a bioactive material for cosmetics or a bioactive material for medicine, but the present invention is not limited thereto. Preferably, the bioactive material may be a water-soluble bioactive material. All types of materials having a bioactive effect may be used as the water-soluble bioactive material. According to one embodiment of the present invention, the water-soluble bioactive material includes peptides. Hereinafter, a peptide will be specifically described as a bioactive material in the detailed description, but the present invention is not limited thereto.

For example, the peptide-based compound may include 2 to 1,000, preferably 2 to 100, and more preferably 2 to 10 amino acids, but the present invention is not limited thereto.

In the peptide-based compound, a peptide refers to a compound in which two or more amino acids are linked via a covalent bond, and exhibits bioactivity in cells and tissues when it is absorbed through the cell membranes. Specific examples of the peptide include a copper peptide (GHK-Cu), alanine/histidine/lysine polypeptide copper HCl, acetyl decapeptide-3, acetyl oligopeptide-2 amide, acetyl tetrapeptide-2, acetyl tetrapeptide-3, acetyl tetrapeptide-5, acetyl tetrapeptide-9, acetyl tetrapeptide-11, acetyl tetrapeptide-15, acetyl tetrapeptide-17, acetyl tetrapeptide-22, acetyl tetrapeptide-40, acetyl tripeptide-1, acetyl pentapeptide-1, acetyl pentapeptide-55amide, acetyl hexapeptide-1, acetyl hexapeptide-8, acetyl hexapeptide-22, acetyl hexapeptide-30, acetyl hexapeptide-37, acetyl hexapeptide-38, acetyl hexapeptide-39, acetyl hexapeptide-49, acetyl hexapeptide-51amide, acetyl heptapeptide-4, acetyl heptapeptide-9, palmitoyl tetrapeptide-3, palmitoyl tetrapeptide-7, palmitoyl pentapeptide-3, palmitoyl pentapeptide-4, palmitoyl pentapeptide-5, palmitoyl tripeptide-1, palmitoyl tripeptide-5, palmitoyl tripeptide-8, palmitoyl tripeptide-29, palmitoyl tripeptide-36, palmitoyl tripeptide-38, palmitoyl tripeptide-40, palmitoyl hexapeptide-12, palmitoyl hexapeptide-14, palmitoyl hexapeptide-15, palmitoyl hexapeptide-56, palmitoyl heptapeptide-5, copper tripeptide-1, oligopeptide-1, oligopeptide-2, oligopeptide-3, oligopeptide-4, oligopeptide-5, oligopeptide-6, oligopeptide-7, oligopeptide-11, oligopeptide-14, oligopeptide-18, oligopeptide-20, oligopeptide-24, oligopeptide-27, oligopeptide-28, oligopeptide-29, oligopeptide-30, oligopeptide-31, oligopeptide-32, oligopeptide-34, oligopeptide-41, oligopeptide-42, oligopeptide-50, oligopeptide-51, oligopeptide-52, oligopeptide-54, oligopeptide-55, oligopeptide-57, oligopeptide-58, oligopeptide-59, oligopeptide-61, oligopeptide-62, oligopeptide-66, oligopeptide-68, oligopeptide-70, oligopeptide-71, oligopeptide-72, oligopeptide-73, oligopeptide-74, oligopeptide-75, oligopeptide-76, oligopeptide-79, oligopeptide-86, oligopeptide-88, oligopeptide-92, RH-oligopeptide-1, RH-oligopeptide-2, RH-oligopeptide-4, RH-oligopeptide-33, tripeptide-1, tripeptide-2, tripeptide-3, tripeptide-29, tripeptide-31, tripeptide-32, tripeptide-47, tripeptide-48, tripeptide-56, tetrapeptide-3, tetrapeptide-4, tetrapeptide-7, tetrapeptide-14, tetrapeptide-21, tetrapeptide-26, tetrapeptide-30, tetrapeptide-32, tetrapeptide-42, tetrapeptide-44, tetrapeptide-51, tetrapeptide-56, tetrapeptide-57, tetrapeptide-58, tetrapeptide-59, nicotinoyl hexapeptide-44, nicotinoyl hexapeptide-45, nicotinoyl hexapeptide-56, nicotinoyl dipeptide-22, nicotinoyl dipeptide-23, nicotinoyl dipeptide-24, nicotinoyl dipeptide-26, nicotinoyl tripeptide-1, nicotinoyl tripeptide-35, nicotinoyl tripeptide-47, nicotinoyl tripeptide-48, nicotinoyl octapeptide-9, nicotinoyl pentapeptide-20, nicotinoyl pentapeptide-33, galloyl nonapeptide-11, galloyl tetrapeptide-19, galloyl tripeptide-47, galloyl tripeptide-48, galloyl tripeptide-35, galloyl tripeptide-7, galloyl pentapeptide-33, galloyl hexapeptide-44, digalloyl tetrapeptide-19, decapeptide-2, decapeptide-4, decapeptide-6, decapeptide-10, decapeptide-11, decapeptide-12, decapeptide-15, decapeptide-16, decapeptide-18, decapeptide-19, decapeptide-20, decapeptide-23, decapeptide-25, decapeptide-28, decapeptide-31, retinoyl tripeptide-1, retinoyl tripeptide-35, retinoyl pentapeptide-4, manganese tripeptide-1, mevalonoyl pentapeptide-37, mevalonoyl pentapeptide-39, mevalonoyl tripeptide-1, mevalonoyl tripeptide-35, mevalonoyl tetrapeptide-36, myristoyl tetrapeptide-6, myristoyl tetrapeptide-8, myristoyl tetrapeptide-34, myristoyl tripeptide-31, myristoyl pentapeptide-8, myristoyl pentapeptide-9, myristoyl pentapeptide-17, biotinoyl tetrapeptide-51, biotinoyl tripeptide-1, biotinoyl tripeptide-35, biotinoyl pentapeptide-4, valprooyl oligopeptide-33, caffeoyl decapeptide-17, caffeoyl oligopeptide-77, caffeoyl tripeptide-1, caffeoyl tripeptide-7, caffeoyl tripeptide-35, caffeoyl pentapeptide-20, caffeoyl pentapeptide-27, caffeoyl hexapeptide-48, caffeoyl hexapeptide-50, caffeoyl hexapeptide-56, caffeoyl hexapeptide-65, caffeoyl heptapeptide-11, SH-polypeptide-1, SH-polypeptide-2, SH-polypeptide-3, SH-polypeptide-4, SH-polypeptide-5, SH-polypeptide-6, SH-polypeptide-7, SH-polypeptide-8, SH-polypeptide-9, SH-polypeptide-10, SH-polypeptide-11, SH-polypeptide-13, SH-polypeptide-15, SH-polypeptide-16, SH-polypeptide-17, SH-polypeptide-18, SH-polypeptide-19, SH-polypeptide-22, SH-polypeptide-25, SH-polypeptide-26, SH-polypeptide-28, SH-polypeptide-29, SH-polypeptide-31, SH-polypeptide-33, SH-polypeptide-34, SH-polypeptide-35, SH-polypeptide-36, SH-polypeptide-37, SH-polypeptide-38, SH-polypeptide-39, SH-polypeptide-40, SH-polypeptide-41, SH-polypeptide-42, SH-polypeptide-43, SH-polypeptide-44, SH-polypeptide-45, SH-polypeptide-46, SH-polypeptide-50, SH-polypeptide-53, SH-polypeptide-54, SH-polypeptide-55, SH-polypeptide-56, SH-polypeptide-58, SH-polypeptide-59, SH-polypeptide-60, SH-polypeptide-62, SH-polypeptide-64, SH-polypeptide-66, SH-polypeptide-70, SH-polypeptide-71, SH-polypeptide-74, SH-polypeptide-78, SH-polypeptide-81, SH-polypeptide-85, RH-polypeptide-1, RH-polypeptide-2, RH-polypeptide-3, RH-polypeptide-4, RH-polypeptide-5, RH-polypeptide-6, RH-polypeptide-7, RH-polypeptide-8, RH-polypeptide-9, RH-polypeptide-10, RH-polypeptide-11, RH-polypeptide-13, RH-polypeptide-14, RH-polypeptide-15, RH-polypeptide-22, RH-polypeptide-26, RH-polypeptide-28, RH-polypeptide-33, RH-polypeptide-51, RH-polypeptide-53, RH-polypeptide-58, RH-polypeptide-59, RH-polypeptide-60, RH-polypeptide-62, RH-polypeptide-64, RH-polypeptide-66, RH-polypeptide-67, nonapeptide-1, nonapeptide-10, nonapeptide-11, nonapeptide-16, nonapeptide-18, nonapeptide-19, oat peptide, soybean polypeptide, dipeptide-1, dipeptide-15, wheat peptide, salicyloyl octapeptide-9, salicyloyl pentapeptide-33, shikimoyl nonapeptide-11, shikimoyl pentapeptide-33, shikimoyl hexapeptide-48, azelaoyl octapeptide-9, azelaoyl tripeptide-1, azelaoyl pentapeptide-37, pea peptide, ursoloyl tetrapeptide-37, ursoloyl tripeptide-1, ursoloyl tripeptide-35, ursoloyl pentapeptide-4, thioctoyl tripeptide-1, thioctoyl tripeptide-35, thioctoyl pentapeptide-4, copper palmitoyl heptapeptide-14, caprooyl tetrapeptide-3, capryloyl dipeptide-17, capryloyl heptapeptide-33, quinoyl tripeptide-1, quinoyl tripeptide-7, quinoyl tripeptide-35, cocoyl pentapeptide-9, coumaroyl nonapeptide-29, coumaroyl dipeptide-3, pentapeptide-3, pentapeptide-13, pentapeptide-18, pentapeptide-20, pentapeptide-27, pentapeptide-28, pentapeptide-31, pentapeptide-36, pentapeptide-37, pentapeptide-44, pentapeptide-45, pentapeptide-46, pentapeptide-48, pentapeptide-54, pentapeptide-56, pentapeptide-57, hexapeptide-2, hexapeptide-3, hexapeptide-9, hexapeptide-10, hexapeptide-11, hexapeptide-12, hexapeptide-17, hexapeptide-33, hexapeptide-42, hexapeptide-43, hexapeptide-47, hexapeptide-57, hexapeptide-61, hexapeptide-62, hexapeptide-63, hexapeptide-65, heptapeptide-10, heptapeptide-12, heptapeptide-13, heptapeptide-16, heptapeptide-22, heptapeptide-36, heptapeptide-37, heptapeptide-38, heptapeptide-39, heptapeptide-40, yeast polypeptide, feruloyl oligopeptide-33, tranexamoyl dipeptide-22, kojyl carboxy dipeptide-23, octapeptide-2, octapeptide-7, octapeptide-8, octapeptide-10, octapeptide-11, octapeptide-15, and the like, but the present invention is not limited thereto.

Also, the bioactive material is not limited as long as it does not hinder the objectives of the present invention, but may have a positive or negative charge in an aqueous solution.

The cationic peptide having positive charges in an aqueous solution may include numerous cationic amino acids, and thus may refer to a peptide that has a pKa of 5 or more, specifically 6 or more, and more specifically 8 or more. More specifically, the positive charges refer to charges measured in a neutral aqueous solution (pH 7). The cationic peptide may preferably include a number of H, K, and R in a peptide sequence. Preferably, the cationic peptide may include two or more amino acids selected from the group consisting of H, K and R. In primary sequences constituting the cationic peptide, the percentage of the cationic amino acids may be greater than or equal to 20%, preferably greater than or equal to 30%, and more preferably greater than or equal to 50%.

An anionic peptide having negative charges in an aqueous solution includes numerous anionic amino acids, and thus may refers to a peptide that has a pKa of 5 or less, specifically 4 or less. More specifically, the negative charges refer to charges measured in a neutral aqueous solution (pH 7). The anionic peptide may preferably include a number of D and E in a peptide sequence. Preferably, the anionic peptide may include two or more amino acid selected from the group consisting of D and E. In primary sequences constituting the anionic peptide, the percentage of the anionic amino acid may be greater than or equal to 20%, preferably greater than or equal to 30%, and more preferably greater than or equal to 50%.

The hydrophilic polymer may have a weight average molecular weight of 10,000 or more, specifically 50,000 or more, and more specifically 100,000 or more and 5,000,000 or less, but the present invention is not limited thereto.

The hydrophilic polymer is not limited as long as it does not hinder the objectives of the present invention, but may include an anionic or cationic polymer, and may have a charge different from that of the bioactive material.

For example, types of anionic groups included in the anionic polymer include a carboxyl group, a sulfate group, a sulfuric ester group, a phosphate group, and the like, but the present invention is not limited thereto. The anionic polymer may be a synthetic polymer, a saccharide-based polymer, polyamino acid-based polymer, and derivatives thereof. One specific example of the anionic polymer may be selected from the group consisting of polyglutamic acid, polyacrylic acid, a carbomer, alginate, carrageenan, hyaluronic acid, poly(styrene sulfonate), carboxymethylcellulose, cellulose sulfate, dextran sulfate, heparin, pectin, heparin sulfate, poly(methylene-co-guanidine), and chondroitin sulfate, but the present invention is not limited thereto.

For example, types of cationic groups included in the cationic polymer include a primary amino group, a secondary amino group, a tertiary amino group, a sulfonium group, a phosphonium group, or the like, but the present invention is not limited thereto. The cationic polymer may be a synthetic polymer, a saccharide-based polymer, a polyamino acid-based polymer, and derivatives thereof. One specific example of the cationic polymer may be selected from the group consisting of polyethyleneimine, polylysine, polyhistidine, polyarginine, polyquaternium-10, and chitosan, but the present invention is not limited thereto.

The aqueous hydrophilic polymer complex solution is not limited as long as it does not hinder the objectives of the present invention, but may exhibit hydrogel properties. A hydrogel is referred to as a hydrated gel. In this case, the hydrogel refers to a hydrated polymer in which a water-soluble polymer has high viscosity via hydrogen bonding, a van der Waals force, hydrophobic interactions, polymer crystallization, or chemical covalent bonding, and has a characteristic of containing a significant amount of water in the aqueous phase. The hydrogel may be generated from various anionic or cationic polymers as described above, may have various chemical compositions, and may also have a structure of a copolymer or a substituted derivative.

More specifically, when a cationic peptide is selected as the bioactive material and an anionic polymer is selected as the hydrophilic polymer, the anionic polymer and the cationic peptide may form an ionic complex, and the cationic peptide may stably exist in the form of a complex with the anionic polymer in the aqueous phase. Preferably, when the cationic peptide includes two or more cationic moieties, the cationic peptide may form two or more ionic bonds with anionic groups of the anionic polymer to form a physical crosslinking point. Therefore, the anionic polymer and the cationic peptide included in the aqueous phase may exhibit a hydrogel property of higher viscosity. Likewise, when the anionic peptide is selected as the bioactive material and the cationic polymer is selected as the hydrophilic polymer, the cationic polymer and the anionic peptide may form an ionic complex, and the anionic peptide may stably exist in the form of a complex with the cationic polymer in the aqueous phase. Preferably, when the anionic peptide includes two or more anionic moieties, the anionic peptide may form two or more ionic bonds with cationic groups of the cationic polymer to form a physical crosslinking point. Therefore, the cationic polymer and the anionic peptide included in the aqueous phase may exhibit a hydrogel property of higher viscosity.

The total number of moles of cationic moieties of the cationic peptide may be the same as or higher than the total number of moles of anionic moieties of the anionic polymer. Preferably, it is desirable that the total number of moles of the cationic moieties is higher than the number of moles of the anionic moieties. As one non-limiting example, the total number of moles of the cationic moieties may be 10- to 100-fold higher than the total number of moles of the anionic moieties. Likewise, the relationship between the total number of moles of the anionic moieties of the anionic peptide and the total number of moles of the cationic moieties of the cationic polymer is as described above, and thus a detailed description thereof will be omitted.

The bioactive material may be included in a range of 0.01% by weight to 50% by weight, specifically in a range of 0.1% by weight to 20% by weight, and more specifically in a range of 0.5% by weight to 10% by weight relative to water serving as the solvent when the aqueous hydrophilic polymer complex solution is produced. Also, the hydrophilic polymer may be included in a range of 0.0001% by weight to 1% by weight, specifically in a range of 0.001% by weight to 0.1% by weight, and more specifically in a range of 0.005% by weight to 0.05% by weight relative to water serving as the solvent, but the present invention is not limited thereto.

After the aqueous hydrophilic polymer complex solution including water, the bioactive material and the hydrophilic polymer within the content ranges as described above is produced, the aqueous hydrophilic polymer complex solution is introduced into a phospholipid solution to generate a colloidal solution.

In the generating of the colloidal solution, the aqueous hydrophilic polymer complex solution exhibiting the hydrogel properties may be introduced into the phospholipid solution so that the phospholipid solution can be hydrated in the aqueous hydrophilic polymer complex solution to form a hydrated liquid crystal phase.

The phospholipids may be selected from natural phospholipids and synthetic lipids. The natural phospholipids may include one or more materials selected from the group consisting of egg yolk lecithin (phospatidylcholine), soybean lecithin, hydrogenated lecithin, lysolecithin, sphingomyelin, phosphatidic acid, phosphatidylserine, phosphatidyl glycerol, phosphatidylinositol, phosphatidylethanolamine, diphosphatidyl glycerol, cardiolipin, and plasmalogen, and the synthetic lipids may include one or more materials selected from the group consisting of dicetyl phosphate, distearoylphospatidylcholine, dioleoylphosphatidylethanolamine, dipalmitoyl phospatidylcholine, dipalmitoyl phosphatidylethanolamine, dipalmitoyl phosphatidylserine, eleostearoylphospatidylcholine, eleostearoylphosphatidylethanolamine, and eleostearoylphosphatidylserine, but the present invention is not limited thereto.

The solvent of the phospholipid solution is not limited as long as it does not hinder the objectives of the present invention, but may include an alcohol. In the present invention, the alcohol may be selected from lower alcohols having 1 to 4 carbon atoms, but the present invention is not limited thereto. One example of the lower alcohol may be methanol, ethanol, propanol, butanol, or the like. More preferably, ethanol may be selected as the lower alcohol. When a lower alcohol is selected, it is desirable in terms of making a lipid membrane of the skin flexible and enhancing an absorption rate of the nano-lipid carrier.

The phospholipids may be included in a range of 0.1% by weight to 50% by weight, specifically in a range of 1% by weight to 40% by weight, and more specifically in a range of 10% by weight to 30% by weight relative to the alcohol serving as the solvent of the phospholipid solution.

The phospholipid solution and the aqueous hydrophilic polymer complex solution may be included in a weight ratio of 1:0.1 to 1:10, specifically in a weight ratio of 1:0.2 to 1:5, and more specifically in a weight ratio of 1:0.5 to 1:2. Preferably, the phospholipid solution and the aqueous hydrophilic polymer complex solution may be mixed at a weight ratio of 1:0.9 to 1:1. At the above mixing weight ratio, the phospholipids may be preferably hydrated by water included in the aqueous hydrophilic polymer complex solution to form a hydrated liquid crystal phase.

As a specific example, as the phospholipid ethanol solution and the aqueous hydrophilic polymer complex solution are mixed, the ethanol included in the phospholipid solution and the water included in the aqueous hydrophilic polymer complex solution are mixed with each other. In the phospholipid solution, the phospholipids form a homogeneous solution in an ethanol solvent, but may be gradually hydrated, when mixed with water, to form a liquid crystal phase, thereby forming a structure of an ethosomal colloid.

An ethosome is a drug carrier used to enhance a skin absorption effect, compared to liposomes. In this case, the ethosome may more easily pass through narrow gaps between the keratinocytes in a state in which its membrane is more flexibly deformed as compared to the liposome, and is produced by dissolving the phospholipids in an ethanol which may serve as a skin penetration enhancer. The ethanol may act with polar head moieties of lipids to reduce interfacial tension, and thus may reduce the interfacial tension of lipid membranes present in the stratum corneum and flexibly form membranes of vesicles themselves. As a result, the ethosome may more effectively deliver the bioactive material into the skin through a skin barrier, which is preferable.

After the aqueous hydrophilic complex solution is introduced into the phospholipid solution to form a colloidal solution, the colloidal solution may be introduced into lipids to form a water-in-oil dispersion.

In the introducing of the colloidal solution into the lipids to form a water-in-oil dispersion, the lipids may be a compound including an aliphatic hydrocarbon which is not miscible with water. In this case, the colloidal solution is introduced into the lipids to form a continuous lipid phase and generate a water-in-oil dispersion in which the colloidal solution forms a dispersed phase. More specifically, the lipids are not limited as long as they do not hinder the objectives of the present invention, but may be a mixed lipid solution including two or more lipids having different melting points, but the present invention is not limited thereto.

The mixed lipid solution may include a first lipid which is in a solid phase at room temperature, and a second lipid which is in a liquid phase at room temperature. Examples of the first lipid which is in a solid phase at room temperature may include one or more materials selected from Apifil (PEG-8 Beeswax), Beeswax, Carnauba wax 2442 L (Copernicia Cerifera wax), Compritol ATO (glyceryl behenate), Cutina CP (cetyl palmitate), Dynasan (trimyristin), glyceryl stearate, glyceryl stearate/malate, glyceryl stearate/acetate, stearic acid, cetyl palmitate, tristearin, and the like, but the present invention is not limited thereto. Examples of the second lipid which is in a liquid phase at room temperature may include one or more materials selected from caprylic/capric triglyceride, paraffin oil, oleic acid, squalene, octyl dodecanol, isopropyl myristate, tocopherol, ethoxydiglycol, dicetyl phosphate, and the like, but the present invention is not limited thereto.

A mixing ratio of the first lipid in a solid phase and the second lipid in a liquid phase is not limited as long as it does not hinder the objectives of the present invention, but the first lipid and the second lipid may be mixed at a weight ratio of 1:0.05 to 1:20, specifically 1:0.1 to 1:10, and more specifically 1:0.5 to 1:5. Preferably, the mixing ratio of the first lipid in a solid phase and the second lipid in a liquid phase may be a weight ratio of 1:0.8 to 1:1.2. Within this range, core portion of the nano-lipid carrier may be stably formed, which is preferable. Because the mixed lipid solution in which the first lipid in a solid phase at room temperature is mixed with the second lipid in a liquid phase at room temperature is included in the form of an oily phase, a nano-lipid carrier having a small particle size may be formed without applying high energy to the mixed lipid solution during homogenization. In this case, the core portion may be stably encapsulated in a shell portion. Also, the hydrophilic polymer complex containing the bioactive material and a hydrophilic polymer corresponding to the core portion and the mixed lipid solution corresponding to the shell portion may form a flowable oil-water interface, and a hydrated liquid crystal phase may be disposed at the oil-water interface by the phospholipids to stabilize the interface very effectively. When only solid-phase lipids are used, a hydrophobic solid-water interface is formed at room temperature without forming the flowable oil-water interface. Therefore, even when the hydrated liquid crystal phase is present at the hydrophobic solid-water interface due to the phospholipids, a stabilization effect of the interface may be somewhat degraded.

The lipids and the colloidal solution may be included at a weight ratio of 1:1 to 1:0.01, specifically a weight ratio of 1:0.8 to 1:0.1, and more specifically a weight ratio of 1:0.7 to 1:0.3, but the present invention is not limited thereto.

The water-in-oil dispersion is not limited as long as it does not hinder the objectives of the present invention, but may be prepared by heating the lipids to form a solution phase, followed by mixing of the colloidal solution. The temperature when heating the lipids may be selected according to the type, molecular weight, and content of the lipids, and the like. Preferably, the temperature may be a temperature greater than or equal to a melting point at which the lipids are converted into a liquid phase. For example, the temperature may be in a range of 50 to 100° C., preferably in a range of 60 to 95° C., and more preferably in a range of 70 to 90° C., but the present invention is not limited thereto.

After the colloidal solution is introduced into the lipids to generate a water-in-oil dispersion, the water-in-oil dispersion may be introduced into an aqueous solution including a surfactant, and homogenized to generate a nano-lipid carrier.

In the introducing of the water-in-oil dispersion into the aqueous solution including the surfactant, followed by homogenization to generate a nano-lipid carrier, the surfactant is not limited as long as it does not hinder the objectives of the present invention, but may include an aliphatic glyceryl-based compound. Preferably, the hydrophile-lipophile balance (HLB) of the surfactant may be greater than or equal to 10. The HLB value is a value that represents a degree of affinity of the surfactant for a hydrophilic material and a lyphophilic material. In this case, the surfactant exhibits lyphophilicity as the HLB value is closer to 0, and exhibits hydrophilicity as the HLB value is closer to 40. An aliphatic glyceryl-based compound having a HLB value of 10 or more, preferably a HLB value of 10 to 25, and more preferably a HLB value of 12 to 20 may be used as the surfactant according to an embodiment of the present invention, but the present invention is not limited thereto. Within this range, stability of the aqueous dispersion may be improved during formation of the nano-lipid carrier, and an effect of further homogenizing the aqueous dispersion may be obtained, which are preferable.

The aliphatic glyceryl-based compound surfactant may be a polyglyceryl-based non-ionic surfactant. One specific example of the aliphatic glyceryl-based compound surfactant may include one or more selected from the group consisting of a polyglyceryl fatty acid ester-based compound, an aliphatic polyglyceryl ether-based compound, polyglyceryl sorbitan fatty acid ester, and a combination of two or more thereof. As one more specific example, the aliphatic glyceryl-based compound surfactant may include one or more selected from the group consisting of polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 mirystate, polyglyceryl-7 mirystate, polyglyceryl-8 mirystate, polyglyceryl-9 mirystate, polyglyceryl-10 mirystate, polyglyceryl-11 mirystate, polyglyceryl-12 mirystate, polyglyceryl-10 oleate, polyglyceryl-11 oleate, polyglyceryl-12 oleate, polyglyceryl-10 stearate, polyglyceryl-11 stearate, polyglyceryl-12 stearate, and a combination of two or more thereof, but the present invention is not limited thereto.

The surfactant may be included at a content of 0.01% by weight to 15% by weight, specifically 0.1% by weight to 10% by weight, and more specifically 0.5% by weight to 5% by weight in the aqueous solution, but the present invention is not limited thereto.

Preferably, the aqueous solution including the surfactant may further include an alcohol. In this case, the alcohol may be selected from lower alcohols having 1 to 4 carbon atoms, and may be preferably ethanol, but the present invention is not limited thereto. When the alcohol is mixed with water, the alcohol forms a water-alcohol cosolvent, and the surfactant takes a form in which the surfactant is dissolved in the cosolvent. A mixing ratio of water and the alcohol in the water-alcohol cosolvent may be in a range of 10:1 to 10:10, specifically in a range of 10:5 to 10:9 based on weight. When the water-alcohol cosolvent is used, a nano-lipid carrier having a smaller particle size may be obtained with low energy during homogenization, and may have high dispersion stability, which are preferable.

The homogenizing step may be performed by homogenizing the nano-lipid carrier at 500 rpm or more, preferably 3,000 to 5,000 rpm for 5 minutes or more, preferably 10 minutes to 20 minutes using a homomixer.

Preferably, the generating of the nano-lipid carrier may further include a high-pressure emulsification step for homogenization. When the nano-lipid carrier is subjected to the high-pressure emulsification step, the nano-lipid carrier may have an appearance of a transparent or suspended liquid phase while containing a relatively high content of the bioactive material, may provide a discriminating sense of use in which the transparent or suspended liquid phase is similarly absorbed into the skin or hair follicles when the transparent or suspended liquid phase is applied onto the skin or hair follicles, compared to when an emulsion is applied onto the skin or hair follicles, and may exhibit superior absorption properties specific for hair follicles, which are preferable.

More specifically, the high-pressure emulsification step may include further homogenizing the nano-lipid carrier by passing the nano-lipid carrier through a high-pressure emulsifier at a pressure of 100 bars or more, preferably 100 to 1500 bars, and more preferably 500 to 1,500 bars at least once, preferably 2 to 5 times. When the nano-lipid carrier is subjected to this step, uniform nanoparticles may be easily formed, and the nano-lipid carrier may be mass-produced, which are preferable.

Hereinafter, the nano-lipid carrier having a bioactive material encapsulated therein according to the present invention will be described in detail.

Referring to FIG. 1, FIG. 1 is a schematic diagram showing one example of a nano-lipid carrier according to the present invention. The nano-lipid carrier according to the present invention includes a core portion including a hydrophilic polymer complex containing a bioactive material and a hydrophilic polymer; and a shell portion disposed on a surface of the core portion and comprising lipids.

Also, the core portion further includes phospholipids. The hydrophilic polymer complex included in the core portion forms an interface with lipids, and a hydrated liquid crystal phase may be disposed at the interface by the phospholipids to very effectively stabilize the interface. Therefore, the bioactive material included in the core portion may not be easily eluted to the outside, may not be eluted into an aqueous solution phase, which is an outer phase, even in a homogenization or high-pressure emulsification step of a production process, and may be present in the shell portion in a state in which the bioactive material is stably encapsulated in the shell portion even when the bioactive material is present in an aqueous dispersion state.

The bioactive material is not limited as long as it does not hinder the objectives of the present invention, but may be included at 0.0001 to 20% by weight, preferably 0.005 to 10% by weight, more preferably 0.002 to 3% by weight, and most preferably 0.001 to 1% by weight in the nano-lipid carrier.

In the hydrophilic polymer complex containing the bioactive material and the hydrophilic polymer, the bioactive material and the hydrophilic polymer may be combined at a weight ratio of 2,000:1 to 20:1, specifically 1,000:1 to 40:1. Within this range, the encapsulation efficiency of the bioactive material may be improved, which is preferable.

The lipids and the phospholipids are not limited as long as they do not hinder the objectives of the present invention, but may be included at a weight ratio of 100:0.1 to 100:50, specifically 100:0.5 to 100:25, and more specifically 100:1 to 100:10.

The nano-lipid carrier is not limited as long as it does not hinder the objectives of the present invention, but may have an average particle size of 20 nm to 1,000 nm, specifically 40 to 700 nm, and more specifically 50 to 500 nm, and may satisfy the following Relationship 1:

$$|T_0 - T_{20}|/T_0 < 0.2 \qquad \text{[Relationship 1]}$$

(wherein T0 represents a transmittance measured at a wavelength of 500 nm after an aqueous dispersion including 1% by weight of a nano-lipid carrier is prepared, and T20 represents a transmittance measured at a wavelength of a 500 nm after the aqueous dispersion including 1% by weight of a nano-lipid carrier is left at 45° C. for 20 days.)

The nano-lipid carrier according to the present invention may have a dispersion stability value of less than 0.1, as specifically defined in Relationship 1. That is, the nano-lipid carrier has excellent dispersion stability, discoloration or phase separation of the nano-lipid carrier does not occur, and the nano-lipid carrier does not have problems such as degraded stability caused by an aggregation phenomenon even when left for a long period of time.

Also, the present invention provides a cosmetic composition including the nano-lipid carrier.

In the present invention, the cosmetic composition is not limited, but may be any one formulation selected from the group consisting of a solution, a suspension, an emulsion, a paste, a gel, a cream, a lotion, a powder, soap, an oil, a powder foundation, an emulsion foundation, a wax foundation, and a spray.

In addition to the nano-lipid carrier serving as the active ingredient, the cosmetic composition may include components commonly used in cosmetics. For example, the cosmetic composition may include conventional adjuvants such as an antioxidant, a stabilizing agent, solubilizing agent, vitamins, a pigment, and a fragrance, and a carrier.

Meanwhile, the cosmetic composition may be produced into any formulation commonly produced in the related art. For example, the cosmetic composition may be formulated into a solution, a suspension, an emulsion, a paste, a gel, a cream, a lotion, a powder, soap, a surfactant-containing cleansing, an oil, a powder foundation, an emulsion foundation, a wax foundation, a spray, and the like, but the present invention is not limited thereto. More specifically, the cosmetic composition may be produced in the form of a lotion, a toner, a face lotion, a nourishing cream, a massage cream, an essence, a pack, a spray, or a powder.

When the formulation of the cosmetic composition is a paste, a cream, or a gel, an animal oil, a vegetable oil, a wax, paraffin, starch, tragacanth, a cellulose derivative, polyethylene glycol, silicone, bentonite, silica, talc, zinc oxide, or the like may be used as a carrier component.

Also, when the formulation of the cosmetic composition according to the present invention is a powder or a spray, lactose, talc, silica, aluminum hydroxide, calcium silicate, or polyamide powder may be used as the carrier component. In particular, when the formulation of the cosmetic composition is a spray, the cosmetic composition may further include a propellant such as chlorofluorohydrocarbon, propane/butane, or dimethyl ether.

In addition, when the formulation of the cosmetic composition according to the present invention is a solution or an emulsion, a solvent, a solubilizing agent, or an emulsifying agent may be used as the carrier component. For example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or a fatty acid ester of sorbitan may be used.

Furthermore, when the formulation of the cosmetic composition according to the present invention is a suspension, water, a liquid-phase diluent (such as ethanol or propylene glycol), a suspending agent (such as ethoxylated isostearyl alcohol, polyoxyethylene sorbitol ester, and polyoxyethylene sorbitan ester), microcrystalline cellulose, aluminum metahydroxide, bentonite, agar, tragacanth, or the like may be used as the carrier component.

As one preferred example, the cosmetic composition including the nano-lipid carrier may be a cosmetic composition for transdermal absorption that has targeting properties for hair follicles.

Because the nano-lipid carrier has a shell portion including the lipids, the nano-lipid carrier may have very superior affinity for hair follicles. Also, because the nano-lipid carrier has a particle size of several tens to hundreds micrometers (nm), the nano-lipid carrier may have an excellent absorption capability specific for the hair follicle, and thus may exhibit excellent targeting properties. Due to these hair follicle targeting properties, the nano-lipid carrier with which the skin is treated may be intensively accumulated in the center of the hair follicle along the hair follicle, and then may be absorbed into the dermis from inside the hair follicles. The nano-lipid carrier absorbed into the dermis may release the bioactive material included in the core portion to give a therapeutic or improvement effect through the bioactive material.

As one non-limiting example, the scalp may be treated with the cosmetic composition for transdermal absorption including the nano-lipid carrier so that the cosmetic composition can target the hair follicles. The treatment may include conventional known methods such as spraying or application. In this case, the cosmetic composition for transdermal absorption may be applied onto the scalp by hand or with an applicator so that the nano-lipid carrier can target the hair follicles present in the scalp. Accordingly, the bioactive material may be supplied to the scalp through hair follicle targeting to give excellent effects of hair growth and prevention of hair loss.

That is, for the purpose of the prevention of hair loss, hair growth, or waxing, there is a great need for a carrier that is not delivered to the percutaneous tissue but is efficiently delivered to the hair follicles in the scalp tissue in which a large number of hair follicles are distributed. Also, the hair follicle is a tissue that may be connected to blood in the fastest manner. The nano-lipid carrier according to the present invention has a particulate phase such as solid lipid nanoparticles, compared to the colloidal carriers such as liposomes, and thus may have an more fast and effective improvement effect when the hair follicles are treated with the nano-lipid carrier.

Hereinafter, the contents of the present invention will be described in further detail with reference to examples thereof. However, it should be understood that the examples are merely for describing the present invention in more detail and are not intended to limit the scope of the present invention.

[Example 1] Production of Nano-Lipid Carrier (NLC)

100 g of a nano-lipid carrier was produced using the production method as follows.

Copper tripeptide-1 (CTP) and alanine/histidine/lysine polypeptide copper HCl (ATP) were added as peptides to purified water, and dissolved to prepare an aqueous peptide solution. The peptides were added so that an amount of the peptides was 0.0225% by weight based on the total amount of the nano-lipid carrier dispersion.

0.1% by weight of an aqueous carbomer solution was added to the aqueous peptide solution, and dispersed at 500 rpm in a 70° C. environment while magnetically stirring. The carbomer was added so that an amount of the carbomer after preparation was 0.000125% by weight, based on the total amount of the aqueous nano-lipid carrier dispersion. An aqueous hydrophilic polymer complex solution in a peptide-hydrogel form was produced through the above process.

To prepare a phospholipid solution, a phospholipid solution was prepared by dissolving hydrogenated lecithin in ethanol. Specifically, ethanol used in the phospholipid solution was prepared so that an amount of the ethanol was 0.8% by weight, based on the aqueous nano-lipid carrier dispersion, and the hydrogenated lecithin was introduced into the ethanol, stirred at 500 rpm and a temperature of 70° C. to completely dissolve the hydrogenated lecithin, and a transparent phospholipid solution was then prepared.

The previously produced aqueous hydrophilic polymer complex solution in the peptide-hydrogel form was added to the phospholipid solution prepared through the above process, and hydrated in the phospholipid solution while mixing at 700 rpm for 5 minutes so that the resulting mixture was prepared in a hydrated liquid crystal phase, thereby forming a core portion to be encapsulated in the nano-lipid carrier.

Next, glyceryl distearate as a first lipid in a solid phase, and caprylic/capric triglyceride as a second lipid in a liquid phase were dissolved while stirring at 70° C. and 500 rpm to prepare a transparent solution phase. A solution including the core portion in the form of a hydrated liquid crystal phase was added to the mixed lipid solution in a transparent solution phase, and stirred at 70° C. and 700 rpm for 10 minutes to prepare a water-in-oil dispersion.

The water-in-oil dispersion was stirred at 2,000 rpm for 15 minutes using a homodisperser (Model 2.5, PRIMIX) while adding the water-in-oil dispersion to a mixed purified water/ethanol solution in which polyglyceryl-10 oleate as a surfactant having a HLB value of 15.9 was dissolved. In this case, the ethanol mixed with the surfactant was mixed so that an amount of the ethanol was 40% by weight, based on the total amount of the aqueous nano-lipid carrier dispersion.

The stirred solution was further homogenized while stirring at 5,000 rpm for 20 minutes using a homomixer. Thereafter, a high-pressure emulsifier (Microfluidics, M-110P microfluidizer) was used for high-pressure emulsification, and homogenization was further performed under conditions of a pressure of 1,000 bars and a pass number of 3. Then, the homogenized solution was slowly cooled at room temperature to finally produce an aqueous nano-lipid carrier dispersion. Contents of the components included in the aqueous nano-lipid carrier dispersion are listed in Table 1.

Example 2

An aqueous nano-lipid carrier dispersion was produced in the same manner as in Example 1, except that the content of ethanol in the solution in which the surfactant was dissolved was reduced to ⅕ so that an amount of the ethanol was 8% by weight, based on the total amount of the nano-lipid carrier. Contents of the components included in the aqueous nano-lipid carrier dispersion are listed in Table 1.

Example 3

An aqueous nano-lipid carrier dispersion was produced in the same manner as in Example 1, except that the carbomer added in Example 1 increased four-fold so that an amount of the carbomer was 0.0005% by weight, based on the total amount of the nano-lipid carrier. Contents of the components included in the aqueous nano-lipid carrier dispersion are listed in Table 1.

Example 4

An aqueous nano-lipid carrier dispersion was produced in the same manner as in Example 1, except that a content of caprylic/capric triglyceride as the second lipid in a liquid phase used in Example 1 was reduced to ½ so that an amount of the caprylic/capric triglyceride was 0.9375% by weight, based on the total amount of the nano-lipid carrier. Contents of the components included in the aqueous nano-lipid carrier dispersion are listed in Table 1.

Table 1 below lists the composition ratios of Examples 1 to 4 as described above, and the presence of homogenization using high-pressure emulsification.

Example 5

An aqueous nano-lipid carrier dispersion was produced in the same manner as in Example 1, except that a homogenization process using the high-pressure emulsification used in Example 1 was omitted.

Comparative Example 1

An aqueous nano-lipid carrier dispersion was produced in the same manner as in Example 1, except that the carbomer as the hydrogel used in Example 1 was not added.

Comparative Example 2

An aqueous nano-lipid carrier dispersion was produced in the same manner as in Example 2, except that sorbitan palmitate was used as the surfactant used in Example 1 instead of polyglyceryl-10 oleate.

Table 2 below lists the composition ratios of Example 5 and Comparative Examples 1 and 2 as described above, and the presence of homogenization.

TABLE 1

| Component Name | Example 1 | Example 2 | Example 3 | Example 4 |
|---|---|---|---|---|
| Copper peptide-1 | 0.0225 | 0.0225 | 0.0225 | 0.0225 |
| Alanine/histidine/lysine polypeptide copper HCl | 0.0025 | 0.0025 | 0.0025 | 0.0025 |
| Carbomer | 0.000125 | 0.000125 | 0.0005 | 0.000125 |
| Purified water | 0.874875 | 0.874875 | 0.8745 | 0.874875 |
| Hydrogenated lecithin | 0.15 | 0.15 | 0.15 | 0.15 |
| Ethanol (for production of phospholipid solution) | 0.8 | 0.8 | 0.8 | 0.8 |
| Glyceryl distearate | 1.875 | 1.875 | 1.875 | 1.875 |
| Caprylic/capric triglyceride | 1.875 | 1.875 | 1.875 | 0.9375 |
| Polyglyceryl-10 oleate | 2.5 | 2.5 | 2.5 | 2.5 |
| Ethanol | 40 | 8 | 40 | 40 |
| Purified water | up to 100 | up to 100 | up to 100 | up to 100 |
| High-pressure emulsification | ○ | ○ | ○ | ○ |

Units: % by weight (based on 100 g of the nano-lipid carrier)

TABLE 2

| Component Name | Example 5 | Comparative Example 1 | Comparative Example 2 |
|---|---|---|---|
| Copper peptide-1 | 0.0225 | 0.0225 | 0.0225 |
| Alanine/histidine/lysine polypeptide copper HCl | 0.0025 | 0.0025 | 0.0025 |
| Carbomer | 0.000125 | — | 0.00025 |
| Purified water | 0.874875 | 0.875 | 0.87475 |
| Hydrogenated lecithin | 0.15 | 0.15 | 0.15 |
| Ethanol (for production of phospholipid solution) | 0.8 | 0.8 | 0.8 |
| Glyceryl distearate | 1.875 | 1.875 | 1.875 |
| Caprylic/capric triglyceride | 1.875 | 1.875 | 1.875 |
| Polyglyceryl-10 oleate | 2.5 | 2.5 | — |
| Sorbitan palmitate | — | — | 2.5 |
| Ethanol | 40 | 40 | 40 |
| Purified water | up to 100 | up to 100 | up to 100 |
| High-pressure emulsification | X | ○ | ○ |

Units: % by weight (based on 100 g of the nano-lipid carrier)

Comparative Example 3

A nano-lipid carrier was produced in the same manner as in Example 1, except that an ethanol solution was used without including the phospholipids of the phospholipid solution used in Example 1.

Comparative Example 4

A nano-lipid carrier was produced in the same manner as Example 1, except that 3.75% by weight of the first lipid in a solid phase was used alone without using the second lipid in a liquid phase in the mixed lipid solution used in Example 1.

Comparative Example 5

A nano-lipid carrier was produced in the same manner as in Example 1, except that 3.75% by weight of the second lipid in a liquid phase was used alone without using the first lipid in a solid phase in the mixed lipid solution used in Example 1.

Characteristics of the compositions were evaluated for each of the experimental groups of Examples and Comparative Examples, as follows.

[Experimental Example 1] Measurement of Particle Size and Transmittance of Nano-Lipid Carrier According to Composition Ratio of Formulation and High-Pressure Homogenization To analyze an average particle size of the nano-lipid carriers produced in Examples and Comparative Examples, the particle sizes of the nano-lipid carriers were measured using a nanoparticle analyzer (Zetasizer Nano ZS, Malvern Instruments), and long-term stability values were calculated from the transmittance (T0) measured at a wavelength of 500 nm after production of the nano-lipid carrier and the transmittance measured at a wavelength of 500 nm after the nano-lipid carrier was left at 45° C. for 30 days using the following Relationship 1. The results are listed in Table 3.

$$|T_0 - T_{20}|/T_0 < 0.2 \quad \text{[Relationship 1]}$$

(wherein T0 represents a transmittance measured at a wavelength of 500 nm after an aqueous dispersion including 1% by weight of a nano-lipid carrier is prepared, and T20 represents a transmittance measured at a wavelength of a 500 nm after the aqueous dispersion including 1% by weight of a nano-lipid carrier is left at 45° C. for 20 days.)

TABLE 3

| | Particle size (nm) | Long-term stability |
|---|---|---|
| Example 1 | 246.1 | 0.081 |
| Example 2 | 102.0 | 0.141 |
| Example 3 | 261.0 | 0.132 |
| Example 4 | 101.5 | 0.154 |
| Example 5 | >5 μm | 0.867 |
| Comparative Example 1 | 1308.0 | 0.498 |
| Comparative Example 2 | >5 μm | 0.772 |
| Comparative Example 3 | 378.2 | 0.245 |
| Comparative Example 4 | 572.2 | 0.792 |
| Comparative Example 5 | 218.2 | 0.855 |

Figure 2:
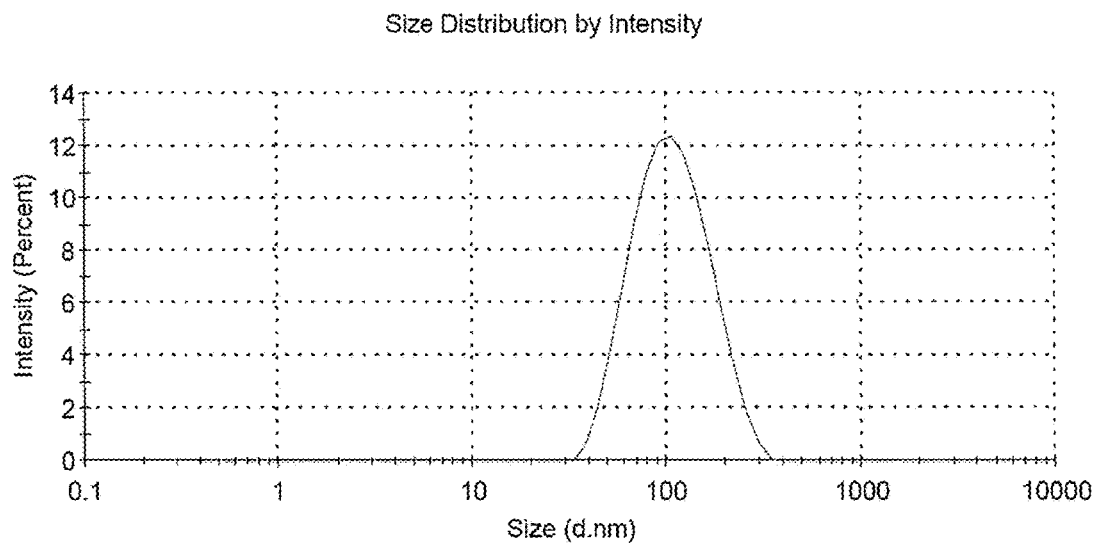
FIG. 2 is a view showing the results of measuring a particle size of the nano-lipid carrier produced according to one embodiment of the present invention.

FIG. 2 is a view showing the results of analyzing the particle size of the aqueous nano-lipid carrier dispersion produced in Example 2.

It was confirmed that the aqueous nano-lipid carrier dispersions produced in Examples 1 to 4 had a particle size of approximately 300 nm or less, and also exhibited excellent long-term dispersion stability. Because the aqueous nano-lipid carrier dispersion produced in Example 5 was not subjected to homogenization using high-pressure emulsification, a suspension having a turbid appearance was obtained, and thus had an average particle size of 5 μm or more, and exhibited poor dispersion stability due to its large particle size.

Meanwhile, it was confirmed that the aqueous nano-lipid carrier dispersions produced in Comparative Examples 1, 2, 4 and 5 were not able to be used as the nano-lipid carrier for cosmetic compositions because nanoparticles having a somewhat large initial particle size were obtained and the aqueous dispersions had poor long-term dispersion stability. In the case of Comparative Example 3, it was observed that nanoparticles having a somewhat large initial particle size were obtained, but the aqueous nano-lipid carrier dispersion exhibited superior long-term dispersion stability, compared to those of the other Comparative Examples.

[Experimental Example 2] Analysis of Stability of Nano-Lipid Carrier

The stabilities of the aqueous nano-lipid carrier dispersions produced in Examples and Comparative Examples were measured. The stability of the produced nano-lipid carrier was measured to check discoloration, phase separation, and the like over time under certain conditions. To measure long-term dispersion stability, each of the aqueous nano-lipid carrier dispersions was disposed in a constant-temperature chamber maintained at 45° C.

Changes in forms of the aqueous nano-lipid carrier dispersions disposed in the constant-temperature chamber were observed with the naked eye at elapsed time points of 1 day, 10 days, 20 days, and 30 days.

Figure 3:
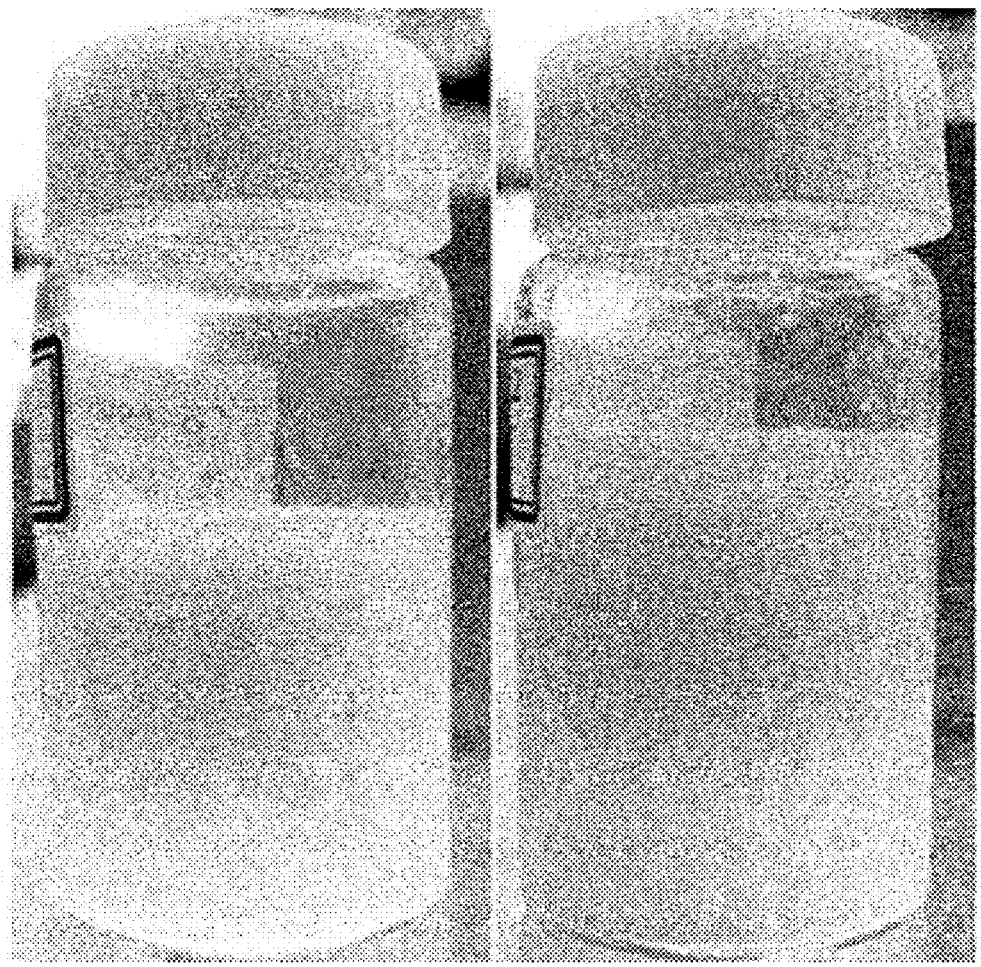
FIG. 3 is a view showing the results of photographing samples after a stability test is performed for 30 days on a nano-lipid carrier dispersion (solid content: 6.5% by weight) according to one embodiment of the present invention.

The results of confirming aggregation, precipitation, and the like of the nano-lipid carrier solution over time are listed in Table 4, and FIG. 3 is an image obtained by photographing the aqueous nano-lipid carrier dispersions of Example 1 and Comparative Example 1, which were left for 30 days in the stability test.

TABLE 4

| | 1 day | 10 days | 20 days | 30 days |
|---|---|---|---|---|
| Example 1 | Stable | Stable | Stable | Stable |
| Example 2 | Stable | Stable | Stable | Aggregated |
| Example 3 | Stable | Stable | Stable | Aggregated |
| Example 4 | Stable | Stable | Stable | Aggregated |
| Example 5 | Aggregated | Precipitated | Precipitated | Precipitated |
| Comparative Example 1 | Stable | Aggregated | Precipitated | Precipitated |
| Comparative Example 2 | Aggregated | Precipitated | Precipitated | Precipitated |
| Comparative Example 3 | Stable | Stable | Stable | Aggregated |
| Comparative Example 4 | Stable | Aggregated | Precipitated | Precipitated |
| Comparative Example 5 | Stable | Precipitated | Precipitated | Precipitated |

Referring to the results of Table 4, the aqueous nano-lipid carrier dispersion of Example 1 exhibited stable dispersion stability up to 30 days, and the aqueous nano-lipid carrier dispersions of Examples 2 to 4 exhibited stable dispersion stability up to 20 days, but appeared to aggregate from day 30. Meanwhile, the aqueous nano-lipid carrier dispersion of Example 5 appeared to precipitate from day 10 because the microparticles having a large initial particle size were produced.

On the other hand, the aqueous nano-lipid carrier dispersions of Comparative Examples 1, 2, 4 and 5 appeared to severely precipitate or aggregate from day 10, and the aqueous nano-lipid carrier dispersion of Comparative Example 3 appeared to aggregate from day 30.

[Experimental Example 3] Measurement of Encapsulation Efficiency of Bioactive Components in Nano-Lipid Carrier Each of the aqueous nano-lipid carrier dispersions produced in Examples and Comparative Examples was centrifuged at 4° C. and 80,000 rpm for 30 minutes using a centrifuge to separate a supernatant and a precipitate. Thereafter, the supernatant was taken to measure a concentration of a non-encapsulated peptide, and a method for calculating the encapsulation efficiency of the non-encapsulated peptide was obtained from Relationship 2 below.

$$EE_{Free} = (W_{Total} - W_{Free})/W_{Total} \times 100 \quad \text{[Relationship 2]}$$

wherein EEFree represents the encapsulation efficiency of a standard material (peptide), WTotal represents the total concentration of the standard material, and WFree represents a concentration of a non-encapsulated standard material. Table 5 below lists the encapsulation efficiencies obtained from the experimental results in numerical terms.

TABLE 5

|  | Encapsulation efficiency (%) |
| --- | --- |
| Example 1 | 93.26 |
| Example 2 | 90.57 |
| Example 3 | 91.21 |
| Example 4 | 89.40 |
| Example 5 | 92.78 |
| Comparative Example 1 | 83.92 |
| Comparative Example 2 | 76.28 |
| Comparative Example 3 | 44.13 |
| Comparative Example 4 | 56.63 |
| Comparative Example 5 | 47.12 |

Based on the results of Table 5, it was seen that the aqueous nano-lipid carrier dispersions of Examples 1 to 5 of the present invention had an excellent encapsulation efficiency of 89% or more, but the aqueous nano-lipid carrier dispersions of Comparative Examples 1 to 5 had significantly reduced encapsulation efficiency.

[Experimental Example 4] Measurement of Nano-Lipid Carrier Particles Specific to Hair Follicles Using Bio-TEM An experiment of measuring the nano-lipid carrier produced in Example 1 using a bio-transmission electron microscope (Bio-TEM; HITACHI H-7650) was performed. A sample solution was sampled through cryogenic treatment using a 200-mesh grid, and measured.

Figure 4:
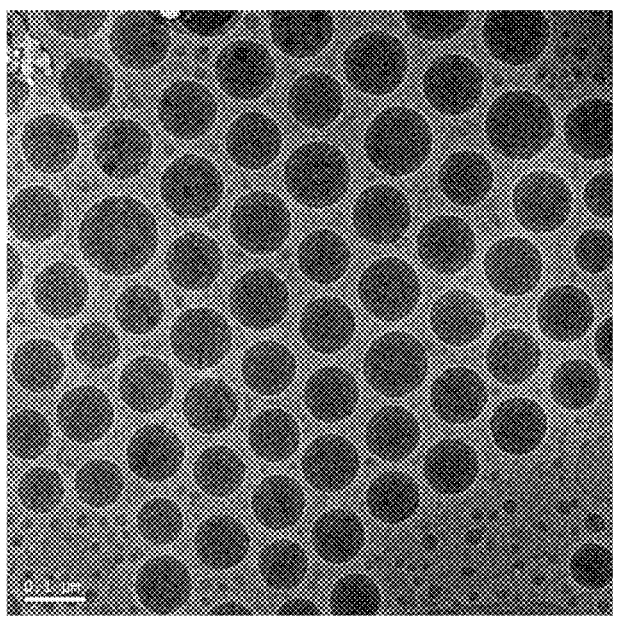
FIG. 4 is a view showing the results of measuring the nano-lipid carrier according to one embodiment of the present invention by bio-TEM (scale bar: 0.1 µm).

The results of measurement of the imaged particles by Bio-TEM are shown in FIG. 4. FIG. 4 shows an image obtained by measuring the nano-lipid carrier on which the grid is seated. As can be seen from these results, it can be seen that the nano-lipid carrier was formed in the form of uniform solid particles having a particle size of approximately 100 nm.

[Experimental Example 5] Measurement of Absorption Behavior of Nano-Lipid Carrier Specific to Hair Follicles Using Confocal Laser Scanning Microscope An experiment of treating the nano-lipid carrier produced in Example 1 with a fluorescent material (i.e., fluorescein isothiocyanate (FITC)) to observe a behavior in which the nano-lipid carrier was absorbed into the skin was performed.

A MicroPig membrane was used for an absorption experiment. The MicroPig membrane was frozen in liquid nitrogen, and then cut into a size of 8 um using a precision microtome. The cut tissue was transferred to a slide glass, and a mounting reagent was applied onto the slide glass. Thereafter, the tissue was observed using a confocal microscope.

Figure 5:
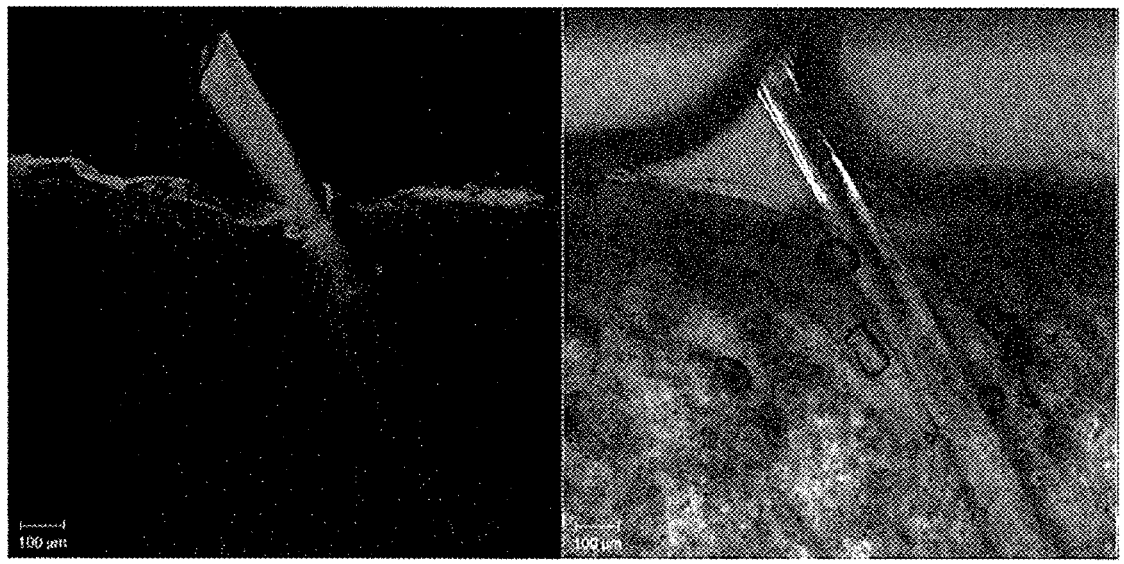
FIG. 5 is a view showing the results of measuring confocal fluorescence for the nano-lipid carrier absorbed into skin hair follicle after the nano-lipid carrier according to one embodiment of the present invention is treated with a fluorescent material (scale bar: 100 µm).

FIG. 5 shows an image obtained by photographing a shape of the FITC-treated nano-lipid carrier which is absorbed into the cut tissue. In general, it can be seen that the nano-lipid carrier was absorbed along the hair follicle. Also, it can be seen that the nano-lipid carrier was slowly absorbed from the inside of the hair follicle toward the dermis.

[Experimental Example 6] Experiment of Skin Absorption Ability of Nano-Lipid Carrier Each of the nano-lipid carrier of Example 1 and an aqueous bioactive material solution was applied onto a MicroPig membrane which was fixed in a skin permeation device (Franz Diffusion Cell) to determine an absorption amount of the nano-lipid carrier.

A nano-lipid carrier permeated through artificial skin was subjected to pretreatment. Specifically, to destroy the nano-lipid carrier permeated through the artificial skin, 1 mL of a sample was added to 2.5 mL of ethanol, 2 mL of chloroform, and 0.5 mL of purified water, and vortexed. Thereafter, the resulting mixture was centrifuged at 4,000 rpm for 10 minutes to extract only a supernatant. An active ingredient was extracted from the pretreated nano-lipid carrier, and then subjected to content analysis using HPLC.

Figure 6:
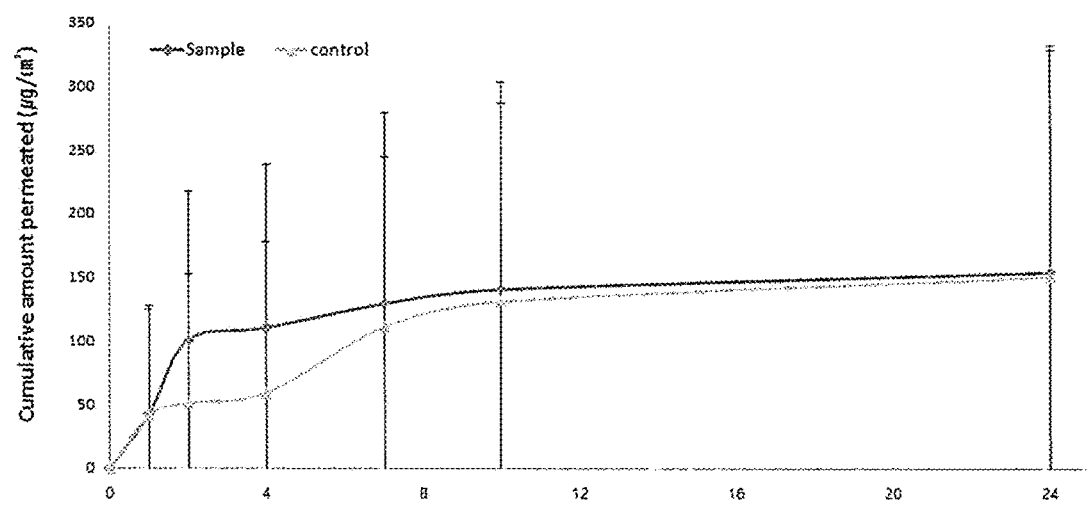
FIG. 6 is a view showing the test results of the nano-lipid carrier according to one embodiment of the present invention which targets the hair follicles so that it is absorbed into the hair follicles.

The results of content analysis using HPLC are listed in Tables 6 and 7 and shown in FIG. 6. Specifically, Table 6 lists the absorption amounts at respective time points.

TABLE 6

|  |  | 0 h | 1 h | 2 h | 4 h | 7 h | 10 h | 24 h |
| --- | --- | --- | --- | --- | --- | --- | --- | --- |
| Example 1 | Average | 0.00 | 42.60 | 100.81 | 110.47 | 129.54 | 140.74 | 154.34 |
|  | Stdev | 0.00 | 85.20 | 116.42 | 128.68 | 150.41 | 163.14 | 178.31 |
| Aqueous bioactive material solution | Average | 0.00 | 41.70 | 50.86 | 59.37 | 111.30 | 131.06 | 150.94 |
|  | Stdev | 0.00 | 83.41 | 101.72 | 118.73 | 133.81 | 155.85 | 178.05 |

TABLE 7

| | Flux (μg/hr * cm²) | $K_p$ (cm/hr * $10^{-4}$) |
|---|---|---|
| Example 1 | 26.61 ± 17.05 | 1,565.02 ± 1002.74 |
| Aqueous bioactive material solution | 19.55 ± 12.48 | 1,303.03 ± 831.74 |

FIG. 6 is a graph for analyzing the absorbed contents of the nano-lipid carrier of Example 1 and the aqueous bioactive material solution over time. It was confirmed that the nano-lipid carrier had a high absorption rate and a rapid absorption time over time in the experimental group in which the nano-lipid carrier was applied. In particular, it was found that the nano-lipid carrier had a new effect of exhibiting an immediate administration effect upon initial administration because the nano-lipid carrier had a cumulative permeation amount twice as fast as that of the control at 2 hours after initial administration.

From the results, it was confirmed that the nano-lipid carrier according to the present invention is able to maintain a stable structure without eluting the bioactive material for a long period of time, and had very excellent encapsulation efficiency of the bioactive material, compared to the control. Also, it was confirmed that the cumulative permeation amount of the nano-lipid carrier was approximately 36% higher when the nano-lipid carrier was administered to the skin, compared to when the bioactive material was directly administered to the skin, and the nano-lipid carrier had a significantly higher (i.e., 2-fold higher) permeation speed when the nano-lipid carrier was administered to the hair follicles, compared to when the nano-lipid carrier was administered to normal skin. From these results, it was confirmed that the nano-lipid carrier of the present invention has an excellent effect as a hair follicle targeting drug carrier.

What is claimed is:

1. A nano-lipid carrier comprising:
   a core portion comprising a hydrophilic polymer complex containing a bioactive material and a hydrophilic polymer; and
   a shell portion disposed on a surface of the core portion and comprising lipids,
   wherein the core portion is in a water-in-oil dispersion and further comprises phospholipids forming a hydrated liquid crystal phase, and the shell comprises a first lipid which is in a solid phase at room temperature, and a second lipid which is in a liquid phase at room temperature.

2. The nano-lipid carrier according to claim 1, wherein the lipids and the phospholipids are included at a weight ratio of 100:01 to 100:50.

3. The nano-lipid carrier according to claim 1, wherein the bioactive material and the hydrophilic polymer are included at a weight ratio of 2,000:1 to 20:1.

4. The nano-lipid carrier according to claim 1, wherein the nano-lipid carrier has an average particle size of 20 nm to 1,000 nm, and satisfies the following Relationship 1:

$$|T0-T20|/T0<0.2 \qquad \text{[Relationship 1]}$$

wherein T0 represents a transmittance measured at a wavelength of 500 nm after an aqueous dispersion including 1% by weight of a nano-lipid carrier is prepared, and T20 represents a transmittance measured at a wavelength of a 500 nm after the aqueous dispersion including 1% by weight of a nano-lipid carrier is left at 45° C. for 20 days.

5. A cosmetic composition comprising the nano-lipid carrier according to claim 1.

6. The cosmetic composition according to claim 5, wherein the nano-lipid carrier has hair follicle targeting properties and the composition is for transdermal absorption.

* * * * *